United States Patent
Van Loenen et al.

(10) Patent No.: US 10,058,324 B2
(45) Date of Patent: Aug. 28, 2018

(54) SUTURE DEVICE

(71) Applicant: Stichting VU-VUMC, Amsterdam (NL)

(72) Inventors: Rianne Irene Van Loenen, Haarlem (NL); Micha Ilan Paalman, Leiden (NL); Alexander Arnold Frederik Adriaan Veenhof, Amsterdam (NL)

(73) Assignee: STICHTING VU-VUMC, Amsterdam (NL)

( * ) Notice: Subject to any disclaimer, the term of this patent is extended or adjusted under 35 U.S.C. 154(b) by 828 days.

(21) Appl. No.: 14/358,136

(22) PCT Filed: Nov. 16, 2012

(86) PCT No.: PCT/NL2012/050811
§ 371 (c)(1),
(2) Date: May 14, 2014

(87) PCT Pub. No.: WO2013/095090
PCT Pub. Date: Jun. 27, 2013

(65) Prior Publication Data
US 2014/0316442 A1   Oct. 23, 2014

Related U.S. Application Data

(60) Provisional application No. 61/560,380, filed on Nov. 16, 2011.

(30) Foreign Application Priority Data

Nov. 16, 2011 (NL) ........................... 2007794

(51) Int. Cl.
*A61B 17/04* (2006.01)
*A61B 17/12* (2006.01)

(52) U.S. Cl.
CPC .... *A61B 17/0469* (2013.01); *A61B 2017/047* (2013.01); *A61B 2017/0472* (2013.01); *F04C 2270/0421* (2013.01)

(58) Field of Classification Search
CPC ............ A61B 17/0469; A61B 17/0491; A61B 17/062; A61B 17/0625; A61B 17/0057;
(Continued)

(56) References Cited

U.S. PATENT DOCUMENTS 5,586,986 A * 12/1996 Hinchliffe .......... A61B 17/0469 112/169
5,860,992 A    1/1999 Daniel
(Continued)

FOREIGN PATENT DOCUMENTS

JP    2005-518862    6/2005
WO    2003073943 A1    9/2003

OTHER PUBLICATIONS

International Search Report and Written Opinion from corresponding foreign application PCT/NL2012/050811, filed Nov. 16, 2012.
(Continued)

*Primary Examiner* — Elizabeth Houston
*Assistant Examiner* — Mohamed Gabr
(74) *Attorney, Agent, or Firm* — Steven M. Koehler; Westman, Champlin & Koehler, P.A.

(57) ABSTRACT

A suture device includes a needle operating device movable longitudinally with respect to a housing between at least an insertion position and a needle transfer position. The needle operating device includes an elongate operating element arranged extending from a distal end of the housing to or near a housing proximal end. A needle holder connected at a distal end of the operating element holds two or more needles, with free ends directed in proximal direction. The holder is movable with respect to a protection device
(Continued)

between at least a protecting position shielding the free ends, and a non-protecting position for the same. A needle receive device at a distal end of the housing receives the free ends when the operating device is moved to the transfer position. In at least the insertion position the holder and the protection device are spaced longitudinally from the housing to receive a tissue therebetween.

24 Claims, 6 Drawing Sheets

(58) Field of Classification Search
CPC ...... A61B 2017/047; A61B 2017/0472; A61B 2017/061; A61B 2017/00637; A61B 2017/00663; A61B 2017/06057; A61B 2017/3492; A61B 6/484; A61F 2/2409
USPC .......................................................... 606/144
See application file for complete search history.

(56) References Cited

U.S. PATENT DOCUMENTS

| | | | |
|---|---|---|---|
| 2003/0167063 A1 | 9/2003 | Kerr | |
| 2005/0119670 A1* | 6/2005 | Kerr | A61B 17/0057 |
| | | | 606/144 |
| 2006/0259046 A1* | 11/2006 | de la Torre | A61B 17/0469 |
| | | | 606/144 |

OTHER PUBLICATIONS

Notice of Reasons for Rejection for Japanese patent application No. 2014-542269, dated Sep. 26, 2016.

* cited by examiner

SUTURE DEVICE

CROSS-REFERENCE TO RELATED APPLICATION

This application is a Section 371 National Stage Application of International Application PCT/NL2012/050811 filed Nov. 16, 2012 and published as WO2013/095090 A2 in English.

BACKGROUND

The discussion below is merely provided for general background information and is not intended to be used as an aid in determining the scope of the claimed subject matter.

The invention relates to a suture device. More particularly, the invention relates to a suture device to suture trocar puncture wounds or such.

With laparoscopic and endoscopic surgery, a small incision or puncture is made in the patient's body to provide access for a tube or a cannula device. A trocar may be provided to make this incision or puncture, and to form a cannula through the incision or puncture. Once extended into the patient's body, the trocar allows for insertion of various surgical instruments such as scissors, dissectors, retractors, or biopsy instruments to perform diagnostics and/or surgery.

Upon completion of the surgical procedure, the remaining puncture wound may require some attention, e.g., in the form of placing sutures to close the wound.

SUMMARY

This Summary and the Abstract herein are provided to introduce a selection of concepts in a simplified form that are further described below in the Detailed Description. This Summary and the Abstract are not intended to identify key features or essential features of the claimed subject matter, nor are they intended to be used as an aid in determining the scope of the claimed subject matter. The claimed subject matter is not limited to implementations that solve any or all disadvantages noted in the Background.

A suture device includes a needle operating device movable longitudinally with respect to a housing between at least an insertion position and a needle transfer position. The needle operating device includes an elongate operating element arranged extending from a distal end of the housing to or near a housing proximal end. A needle holder connected at a distal end of the operating element holds two or more needles, with free ends directed in proximal direction. The holder is movable with respect to a protection device between at least a protecting position shielding the free ends, and a non-protecting position for the same. A needle receive device at a distal end of the housing receives the free ends when the operating device is moved to the transfer position. In at least the insertion position the holder and the protection device are spaced longitudinally from the housing to receive a tissue therebetween.

Needle protection holes can be arranged at 90 degrees rotated with respect to the needle receiver. During insertion of the suture device in a puncture wound, the needles are positioned in the needle protection holes, so that the needles do not damage any tissue during insertion of the device. When the suture device is located at the desired location in the puncture wound, the needle operating device is pushed distally with respect to the housing to move the needles out of the needle protection holes and past the puncture wound. Then, the operating device has to be rotated over an angle of 90 degrees to align the needles with the needle receiver. Subsequently the needles are pulled back towards the housing to push the free needle ends through the tissue surrounding the puncture wound and in the needle receiver to transfer the needles from the needle holder to the housing.

Once the needles are transferred from the needle operating device to the housing, the housing and the needle operating device may be removed from the puncture wound, while leaving the suture material in the tissue. Thereafter, the suture material may be tied to a knot to close the puncture wound.

In the insertion position of the needle operating device, the needle holder and the needle protection device are spaced from the housing. Tissue to be sutured can be received in the space between the housing and the combination of needle holder and needle protection device. The insertion position of the suture device is the state in which the suture device is introduced into the patient's body until the suture device is correctly positioned with respect to the tissue to be sutured. In this insertion position, at least the free ends of the needles are shielded by the needle protection device, i.e. the needle holder is in the protecting position with respect to the needle protection device.

It has been found that, in particular in the case of a trocar puncture wound, the fascia surrounding this wound has sufficient elasticity and tension to draw itself into the space between the housing and the needle holder and needle protection device. The entering of the fascia in the space between the housing and the needle holder and needle protection device can well be felt by the user of the suture device. This makes reliable positioning of the suture device in a trocar puncture wound or a similar wound in at least the longitudinal direction possible.

Further, once the suture device is placed in the correct position with respect to the puncture wound, i.e. when the tissue to be sutured has entered the space between the needle holder and the housing, the needle holder only has to be moved proximally from the insertion position towards the housing to transfer the needles from the needle holder through the tissue and into the needle receive device. There is no rotation of the needles or movement of the needle holder in the distal direction required to transfer the needles from the needle holder to the needle receive device.

During the movement of the needle operating device from the insertion position to the needle transfer position, the needle holder can be moved with respect to the needle protection device from the needle protecting position towards the non-protecting position, so that the free ends of the needles, e.g. sharp needle tips, are no longer protected by the needle protection device and can be pierced through the tissue to be sutured arranged in the space between the housing and the combination of the needle holder and needle protection device.

Further, during the movement of the needle operating device from the insertion position to the needle transfer position, the needles will move within the space which was already occupied by the suture device in the insertion position. Therewith, the risk of any damage to other tissue or organs is substantially reduced.

In an embodiment, a cross sectional dimension of the operating element arranged, in the insertion position, between the housing and the needle holder is substantially smaller than a cross sectional dimension of the needle holder and a cross-sectional dimension of the housing.

According to an aspect of invention, the space between the needle holder and the housing can be used to receive tissue to be sutured therebetween so that a movement of the needles parallel to the longitudinal axis can be used to transfer the needle from the needle holder to the needle receive device. By using an operating element with a cross section between the housing and the needle holder which is substantially smaller than a cross sectional dimension of the needle holder and a cross-sectional dimension of the housing, a relative large space can be obtained to receive the tissue to be sutured in this space. Furthermore, it is desirable that the operating element in the space runs substantially over the longitudinal axis of the suture device so that the space has substantially the same volume at opposite sides of the operating element.

Since the space between the needle holder and the needle protection device is used for passing the needles from the needle holder to the needle receive device, the needles can be straight needles arranged substantially parallel to a longitudinal axis of the housing.

In an embodiment, the housing comprises a longitudinal channel to enclose the operating element, wherein the channel is an open channel. When the needles are transferred from the needle holder to the needle receive device, the housing can be pulled out in proximal direction to pull the needles and the suture material through the tissue to be sutured and out of the patient's body. It is advantageous that at the same time the needle operating element can remain in substantially the same position so that the needle holder can feed the suture material from internally. By providing an open channel the operating element can be enclosed in the housing during insertion and transfer of the needles from the needle holder to the needle receive device, and thereafter the operating element can easily move out of the enclosure of the housing when the housing is pulled back in proximal direction.

To prevent that the operating element prematurely is released from the open channel, a holding device may be provided in the open channel. Such holding device may for instance be an open ring shaped spring element which will hold the operating element until it is pulled out of the open ring. Pulling out may require a substantial force so that premature release is avoided.

In an embodiment, the needle holder comprises a first needle holder part and a second needle holder part, wherein the first and second needle holder parts are configured to hold the needles therebetween, wherein the first needle holder part is operatively connected to the operating element, and wherein the second needle holder part supports the needle protection device, and wherein the first and second needle holder parts are movable with respect to each other in order to displace the needles with respect to the needle protection device and to release the needles from the needle holder when the free ends of the needles are received by the needle receive device.

The first and second needle holder parts can be used to hold the needles therebetween, and relative movement of the needle holder parts can be used to push the needles through the space where the tissue to be sutured is arranged. The first needle holder part may be provided with a stop element against which the clamped ends of the needles rest to ensure that the needles will move with the movement of the first needle holder part. The second needle holder part supports the needle protection device. The second needle holder part and the needle protection device may be configured as an integral part.

In an embodiment, the needle protection device encloses, in the protection position, at least partially the needles, preferably the whole needles. In such embodiment, the needle protection device may be a sleeve-like element enclosing, in the protecting position, the needle holder and the needles held by the needle holder. The sleeve-like element may be configured from one or more parts.

In an alternative embodiment, the needle protection device comprises one or more elements arranged, in the protection position, next to the free ends of the needles so that these needle ends normally cannot damage any organ or tissue within the body. Any other embodiment of a needle protection device may also be applied.

In an embodiment, the needle receive device comprises a sleeve and a flexible disc-shaped element arranged in the sleeve, wherein the disc shaped element and sleeve are designed to catch a needle therebetween. It has been found that a disc shaped element arranged in a sleeve may be used to catch the needles. The free needle ends may relatively easily be pushed between the disc shaped element and the sleeve, while movement of the needles in the opposite direction, once caught between the disc shaped element and the sleeve, is relatively difficult. To increase the catching effect of this construction, the disc shaped element may be curved in radial direction, with the convex side towards the needle holder. Also, the needles, the sleeve and/or disc shaped element may be provided with friction increasing material or a profile, such as small ribs or teeth to improve the catching effect of the needle receive device.

The disc shaped element may be a separate element mounted in the needle receive device or the disc shaped element may be an integral part of a component of the suture device.

In an embodiment, the needle holder comprises a suture material storage space for storing suture material. A substantial length of suture material may be required to be able to place a suture. For example, a suture thread may be attached to both needles of the suture device. When the needles are pierced through the tissue to be sutured, the needles can be pulled out of the patient's body leaving a loop of suture material from outside the patient's body running through the tissue at opposite sides of the puncture wound.

Before the needles are pulled out of the patient's body, the suture material is preferably stored in a storage space for suture material so that it does not interfere with the operation of the suture device. The storage space for suture material may for instance be provided in a hollow channel in the operating element. In an alternative embodiment, the storage space may be formed in the needle holder, for example by grooves arranged in one or more parts of the needle holder.

In an embodiment, the needle operating device and the housing are constrained in a rotational position with respect to each other. It may be of importance that the needles and needle receive device are properly aligned with respect to each other for successful transfer of the needles from the needle holder to the needle receive device. Also it is of importance that the needles are properly aligned with the puncture wound. To avoid any misalignment between the housing and the needles, it is advantageous that the housing and needle operating device are constrained with respect to each other in a rotational position.

In an embodiment, the suture device comprises one or more coupling elements to couple the suture device to a trocar. The suture device may advantageously be configured to be connected to a trocar, in particular the trocar with which the puncture wound to be sutured is made. A trocar may be any cannula device used in laparoscopic and endoscopic surgery to provide access into the patient's body. Preferably, the trocar is a cannula device which remains in the body after creating a puncture wound by a cutting device arranged and connected to in the trocar. After creation of the puncture wound, the cutting device is removed from the cannula device. Trocar may also refer to the combination of cannula device and cutting device.

When the rotational position of the trocar with respect to the puncture wound is remained during the surgical procedure and/or when this orientation during puncture is registered, for instance by providing a mark on the patient's body, the rotational position of the trocar is representative for the orientation of the puncture wound. By placing the suture device in a fixed orientation with respect to the trocar the suture device can easily be placed in a correct rotational position with respect to the puncture wound, i.e. the needles can properly be aligned with the tissue at opposite sides of the puncture wound.

When during cutting the cutting device is not fixed with respect to the trocar, or when no trocar is used, the rotational position of the cutting device during cutting may be registered, for instance by providing a mark on the trocar or the patient's body, so that the orientation of the puncture wound is known during insertion of the suture device into the puncture wound.

In an embodiment, a first coupling element is provided on the housing to couple the housing to the trocar, and a second coupling element is provided on the needle operating device to couple the needle operating device to the trocar. When both the housing and the needle operating device are provided with a coupling element that can be coupled to the trocar, each of these parts can be held in its position by coupling that part to the trocar, while the other part can be manipulated by the user. The coupling elements may be designed as any coupling element capable of being coupled to the trocar. The coupling elements are preferably designed similar to known coupling elements to couple one or more devices to a trocar, such as a cutting device to create the puncture wound.

The suture device may be designed to be coupled to trocars known in the field. As an alternative, a new trocar design may be contemplated to cooperate with the suture device of the invention.

In an embodiment, the suture device, for example the needle holder and/or the housing, comprises a part, for example an extension, having a non circular cross section to determine a rotational position of the needle operating device and/or housing with respect to a non-circular puncture in which the suture device is arranged. It is of importance that at least the needle operating device is properly aligned with the usually slit shaped puncture wound so that the needles will be deployed at opposite sides of the puncture wound, at two locations on a line substantially perpendicular to the direction of the slit shaped wound.

To ensure correct positioning of the needle operating device, the suture device may comprise a positioning part having a non circular cross section. When this positioning part is arranged in the puncture wound, the tension in the tissue to be sutured may provide feedback on the rotational position of the positioning part in the puncture wound. The puncture wound may push the positioning part in the position wherein the longest dimension corresponds with the direction of the slit shaped wound. The suture device may be designed such that the needles will be optimally positioned for this orientation of the positioning part, i.e. the needles are arranged to pierce the tissue to be sutured on a line perpendicular to the main direction of the puncture wound.

The positioning part may for example be arranged in the space between needle holder and needle receive device or at the distal end of the suture device.

As an additional or an alternative embodiment, the trocar may be provided with a non circular positioning part to maintain the rotational position of the trocar in the puncture wound.

In an embodiment, the suture device comprises a spacer device configured to ensure a minimum distance between the needle protection device and the housing. A spacer device may be provided between the needle protection device and the housing to prevent that tissue to be sutured is clamped between the needle protection device and the housing and is pressed out of the space between the needle protection device and the housing as a result of this clamping. This spacer device may for example be a bushing provided on the operating element between the needle protection device and the housing.

In an embodiment, the suture device is dimensioned to suture trocar puncture wounds of at least 8 mm, preferably at least 10 mm.

An aspect of the invention further provides a combination of a suture device and a trocar, wherein the trocar and suture device are configured to be coupled to each other in a fixed rotational position.

BRIEF DESCRIPTION OF THE DRAWINGS

An embodiment of a suture device according to the invention will now be described in further detail, by way of example only, with reference to the accompanying drawings, in which.

DETAILED DESCRIPTION

Figure 1:
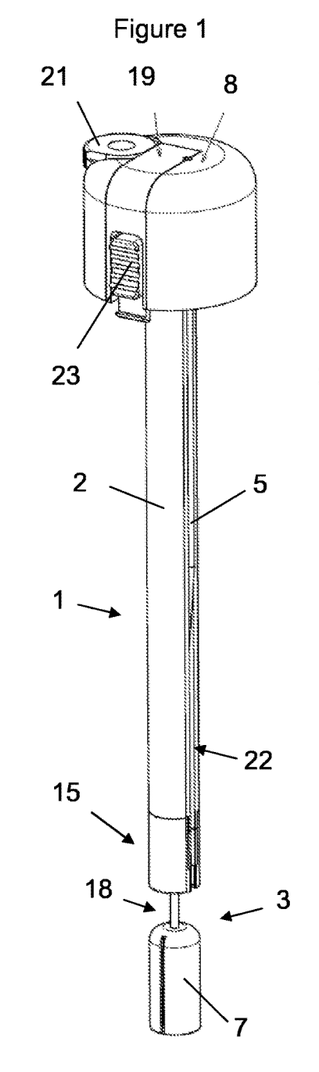
FIG. 1 shows a perspective view of a suture device.
Figure 2:
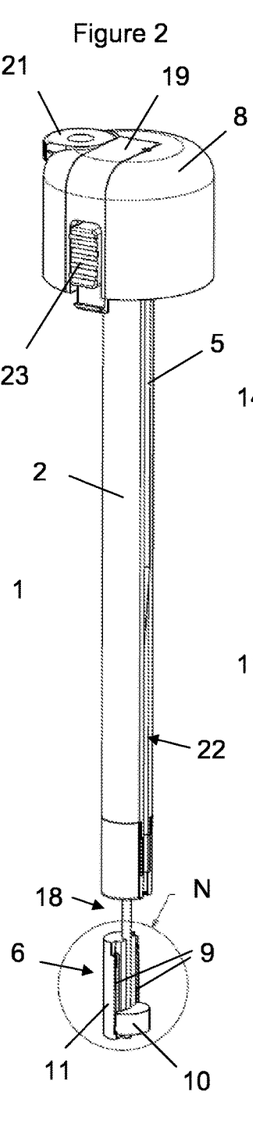
FIG. 2 shows a perspective view of the suture device of FIG. 1 without the needle protection element.

FIGS. 1 and 2 show a suture device, generally denoted by reference numeral 1. The suture device 1 comprises an elongate housing 2 and a needle operating device 3. The elongate housing 2 and the needle operating device 3 are movable with respect to each in a longitudinal direction of the suture device 1.

The suture device 1 is designed to suture trocar puncture wounds, resulting from laparoscopic and/or endoscopic surgery.

The needle operating device 3 comprises an operating element 5, a needle holder 6, and a needle protection element 7.

The operating element 5 comprises an elongate rod shaped element which runs from a distal end of the suture device 1 to a proximal end thereof. A distal end of the operating element 5 is connected to the needle holder 6 and at the proximal end of the operating element 5 an operating portion 8 configured for operating the suture device 1 is provided.

In the middle part of the operating element 5 two bends are provided so that at the distal end of the suture device 1, the operating element 5 is located on the longitudinal axis of the suture device 1, while near the proximal end of the suture device 1, the operating element 5 is arranged spaced from the longitudinal axis of the suture device 1 and at the circumference of the housing 2.

Two straight needles 9 are held at one end by the needle holder 6. The free ends of the needles 9 extend in proximal direction of the suture device 1, i.e. towards the housing 2. In the insertion position of the suture device 1 as shown in FIG. 1, the needle protection element 7 encloses the needles 9 held by needle holder 6. The needles 9 are connected to suture material (not shown). The needle protection element 7 is a sleeve like element. The proximal edge of the needle protection element 7 is rounded off to avoid the risk that this end of the needle protection element 7 causes any damage to organs or tissue within the patient. When desired the distal edge of the needle protection element 7 may also be rounded off for this reason.

Figure 3:
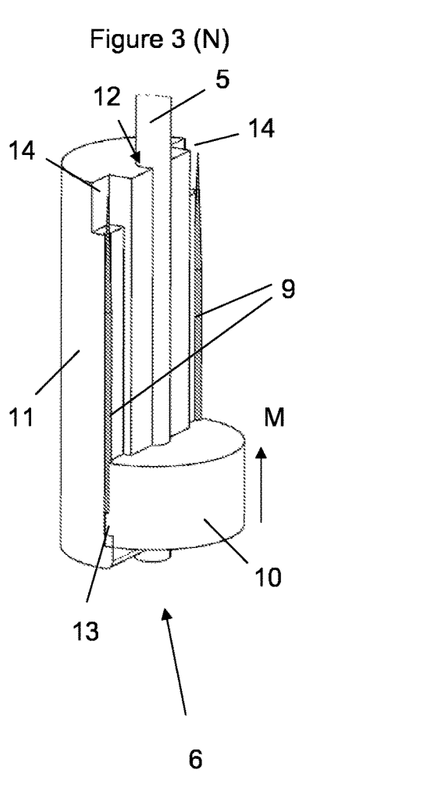
FIG. 3 shows a detail of the distal end of the suture device as shown in FIG. 2.

The needle holder is shown in more detail in FIG. 3. In FIGS. 2 and 3, the needle protection element 7 is not shown.

The needle holder 6 comprises a first needle holder part 10 and a second needle holder part 11. The first needle holder part 10 is connected to the operating element 5 so that by manipulation of the operating portion 8 the position of the first needle holder part 10 can be controlled. The second needle holder part 11 supports the needle protection element 7. The second needle holder part 11 further comprises a channel 12 through which the operating element 5 is guided, such that the first needle holder part 10 and the second needle holder part 11 are only movable with respect to each other in the longitudinal direction of the suture device 1, indicated by arrow M by a sliding movement of the second needle holder part 11 over the operating element 5.

The first needle holder part 10 and the second needle holder part 11 each have a half cylindrical shape, wherein the length of the second needle holder part 11 is at least the length of a needle 9 and substantially larger than the length of the first needle holder part 10.

The needles 9 are clamped between the first needle holder part 10 and the second needle holder part 11. The first needle holder part 10 and the second needle holder part 11 are provided with grooves to keep the needles 9 in a proper alignment with respect to the longitudinal axis of the suture device 1.

The first needle holder part 10 comprises a stop 13. The clamped needle ends are placed against this stop 13 so that during a relative movement of the first needle holder part 10 with respect to the second needle holder part 11 in the direction M, the needles 9 are pushed by the first needle holder part 10 to move together with the first needle holder part 10 in a longitudinal direction.

At the distal end of the second needle holder part 11 another stop is provided to limit a relative movement of the needle holder part 10 in a direction opposite to the direction indicated by M.

Since the needle protection element 7 is supported by the second needle holder part 11, the needles 9 will, during this movement, also move with respect to the needle protection element 7 so that the free ends of the needles can be moved from a protected position, wherein the needles are completely enclosed by the needle protection element 7 to an unprotected position wherein the free ends of the needles 9 at least partially extend outside the needle protection element 7.

Figure 4:
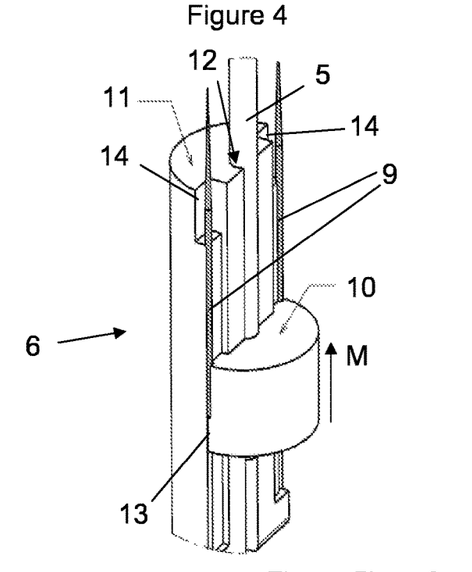
FIG. 4 shows the distal end of the suture device with needles moved in the proximal direction.

FIG. 4 shows that the first needle holder part 10 is moved in longitudinal direction M so that the needles 9 have been displaced with respect to the second needle holder part 11.

The second needle holder part 11 comprises at its proximal ends two recesses 14. The grooves in the second needle holder part 11 for guiding the needles 9 end in these recesses 14. When the stop 13 pushes the distal needle ends of the needles 9 up to the recesses 14, the needles 9 will no longer be clamped between the first needle holder part 10 and the second needle holder part 11, and thus the needles 9 will no longer be held by the needle holder 6.

The housing 2 is substantially formed by a cylindrical body comprising at a distal end a needle receive device 15 capable of receiving and holding the free ends of the needles 9 once inserted into the needle receive device 15.

Figure 5A:
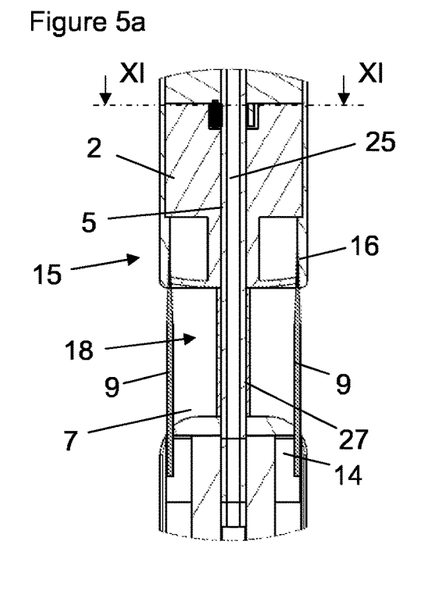
FIG. 5a shows a cross section of the needle receive device extending from the needle protection.
Figure 5B:
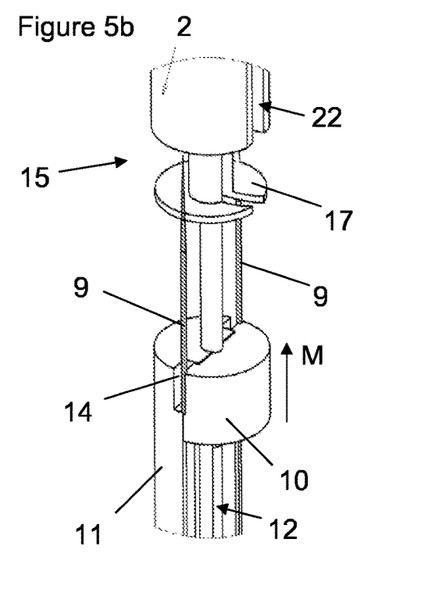
FIG. 5b shows a perspective view of the needle receive device without the sleeve.

The needle receive device 15 comprises a sleeve 16 and a curved disc 17 of flexible material. A cross-section of the needle receive device 15 is shown in FIG. 5*a*. FIG. 5*b* shows a perspective view of the needle receive device 15 without the sleeve 16.

The flexibility and shape of the disc 17 is selected such that a needle 9 can easily pass between the disc 15 and the sleeve 16 when moved in the direction M, but is very hard to pull back in the opposite direction.

It is remarked that the needles 9, the sleeve 16 and/or disc 17 may be provided with friction increasing material or a profile, such as small ribs or teeth to improve the catching effect of the needle receive device 15.

The needles 9, the needle holder 6, and the distance between the needle holder 6 and the needle receiving device 15 are configured such that the free needle ends are caught by the needle receive device 15 before the opposite needle ends are released from the needle holder 6, so that a reliable transfer of the needles from the needle holder 6 to the needle receive device 15 is ensured.

A bushing 27, as shown in FIG. 5*a*, can be arranged, as a spacer between the needle protection element 7 and the housing 2 to ensure a minimum distance between the needle protection element 7 and the housing 2.

In an embodiment, the suture device 1, for example the needle holder 11 and/or the housing 2, comprises a part, for example an extension 7A,2A having a non circular cross section to determine a rotational position of the needle operating device 3 and/or housing 2 with respect to a non-circular puncture in which the suture device 1 is arranged. It is of importance that at least the needle operating device 3 is properly aligned with the usually slit shaped puncture wound so that the needles 9 will be deployed at opposite sides of the puncture wound, at two locations on a line substantially perpendicular to the direction of the slit shaped wound.

To ensure correct positioning of the needle operating device 3, the suture device 1 may comprise the positioning part 2A, 7A having a non circular cross section. When this positioning part 2A, 7A is arranged in the puncture wound, the tension in the tissue to be sutured may provide feedback on the rotational position of the positioning part 2A, 7A in the puncture wound. The puncture wound may push the positioning part 2A, 7A in the position wherein the longest dimension corresponds with the direction of the slit shaped wound. The suture device 1 may be designed such that the needles 9 will be optimally positioned for this orientation of the positioning part 2A, 7A i.e. the needles 9 are arranged to pierce the tissue to be sutured on a line perpendicular to the main direction of the puncture wound The positioning part 2A, 7A may for example be arranged in the space between needle holder 11 and needle receive device 15 or at the distal end of the suture device.

In the insertion position of the suture device 1 as shown in FIGS. 1 and 2, a space 18 is formed between the distal end of the housing 2 and the proximal end of the combination of the needle holder 6 and the needle protection element 7. In this space 18 only the operating element 5 runs from the needle holder 6 towards the operating portion 8. However, since the cross section of the operating element in this space 18 is substantially smaller than the cross section of the distal end of the housing 2 and/or the proximal end of the combination of the needle holder 6 and the needle protection element 7, this space 18 can be used to receive tissue to be sutured therein.

At the proximal end of the housing 2 an operating part 19 is provided which closely fits in a recess 20 in the operating portion 8. When the operating part 19 is arranged in the recess 20 the relative rotational position of the housing 2 and the needle operating device 3 is fixed. The operating portion 8 is provided with a rotary button 21 which is rotatable between a locked position in which the operating portion 8 and the operating part 19 are not movable with respect to each other, and an unlocked position in which the operating portion 8 and the operating part 19 are movable with respect to each other in the longitudinal direction. Any other suitable locking device to lock the relative positions of the operating portion 8 and the operating part 19 may also be applied.

Figure 11:
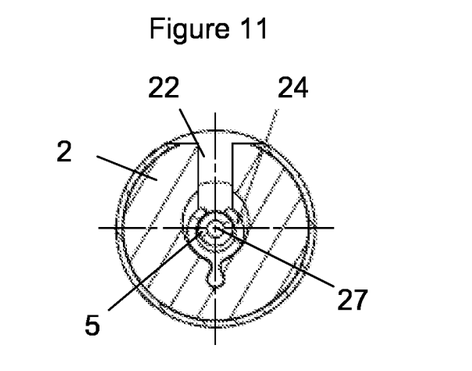
FIG. 11 shows a cross section of FIG. 5a along the line XI-XI.

The housing 2 further comprises an open channel 22 through which the operating element 5 is guided. A holding device 24 is provided in the open channel 21 to hold the operating element 5 in its position with respect to the channel 21. This holding device 24 is designed to hold and align the operating element 5 on the longitudinal axis. FIG. 11 shows a cross section of the suture device 1 showing the holding device 24. Any other holding device that can be used to hold the operating element 5 until decoupling between the needle operating device 3 and the housing 2 is desired, can also be applied.

The holding device 24 comprises an open ring shaped spring device such that the operating element 5 can be pulled out of the holding device 24 and taken out of the open channel 22 during placement of a suture in a tissue to be sutured. It is remarked that due to the double bended design of the operating element 5, the housing 2 can be removed in the proximal longitudinal direction from the operating element 5, whereby when sufficient puling force is exerted on the housing 2, the holding device 24 will be pulled from the operating element 5.

Figure 6:
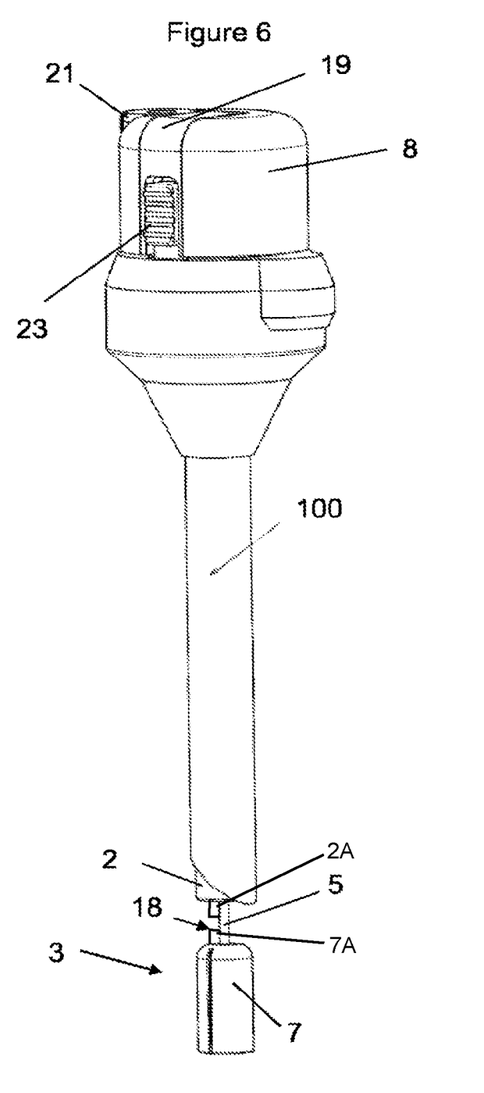
FIG. 6 shows the suture device of FIG. 1 arranged in a trocar.

The suture device 1 shown in FIG. 1 is designed to be used in combination with a trocar 100. In FIG. 6, the suture device 1 is shown arranged in a trocar 100. The operating portion 8 and the operating part 19 are arranged at the proximal end of the trocar 100. The needle holder 6, needle protection element 7, and the space 18 extend from the distal end of the trocar 100. The operating portion 8 and the operating part 19 each comprise a pivotable push button 23 having a latch, with which the operating portion 8 and the operating part 19 can be releasably coupled to the trocar 100. The trocar 100 is also used for creating the puncture wound by a cutting device coupled to the trocar 100, and removed after creation of the puncture wound. As a result, the orientation of the slit shaped puncture wound can be recognized from the rotational position of the trocar 100 during creation of the puncture wound.

When the orientation of the trocar 100 with respect to the puncture wound is remained during the surgical procedure and/or when this orientation during puncture is registered, for instance by providing a mark on the patient's body, the rotational position of the puncture wound is known. By placing the suture device 1 in a fixed rotational position with respect to the trocar 100 the suture device 1 can be placed in a correct orientation with respect to the puncture wound, i.e. the needles 9 are aligned with the tissue at opposite sides of the slit shaped puncture wound.

Further, it has been found that the space 18 of the suture device 1 can effectively be used to determine whether the suture device 1 is properly positioned in longitudinal direction with respect to the tissue to be sutured, as will be described hereinafter.

When it is desired to suture a puncture wound, for example a slit shaped wound in the fascia of the abdominal wall, the following procedure can be followed.

While the trocar 100 still extends through the puncture wound, the suture device 1 can be placed in the trocar 100. The suture device 1 is connected to the trocar 100 by the latches of the pivotable push buttons 23 so that the suture device 1 is properly aligned with the trocar 100 in both longitudinal and rotational positions.

The combination of suture device 1 and trocar 100 can be pulled out of the puncture wound until the tissue to be sutured may enter into the space 18. Due to the flexibility and tension of the fascia, the tissue surrounding the puncture wound will snap into the space 18. This entering of the tissue into the space 18 can very well be felt by the surgeon operating the suture device 1. As a result, the surgeon will know when the suture device 1 is properly aligned in longitudinal direction with respect to the puncture wound. No additional camera is required. Further, the rotational position of the suture device is also adapted to the puncture wound by maintaining the rotational position of the trocar 100 or by rotating the trocar 100 back to the rotational position in which the puncture was made with the trocar 100.

Once the tissue to be sutured is arranged in the space 18 between the needle receive device 15 and the combination of needle holder 6 and needle protection element 7, the suture device 1 can be operated to transfer the needles 9 from the needle holder 6 through the tissue to be sutured to the needle receive device 15.

To make relative movement of the needle operating device 3 with respect to the housing 2 possible, the rotary button 21 is rotated from the locked to the unlocked position. Subsequently, the operating portion 8 may be uncoupled from the trocar 100 by actuating the associated pivotable push buttons 23, and may be moved in proximal direction with respect to the operating part 19 and housing 2.

When no bushing 27 or other spacer device is present between the needle protection element 7 and the housing 2, this movement will result in that the combination of needle holder 6 and needle protection element 7 move towards the needle receive device 15 until the tissue to be sutured in the space 18 is clamped between the needle protection element 7 and the needle receive device 15. However, this clamping of tissue may, in some applications, result in that the tissue to be sutured is pressed out of the space 18 which is undesirable.

To avoid the risk that tissue to be sutured is pressed out of the space 18 when the needle protection element 7 and the housing 2 are pulled towards each other, the bushing 27 can be provided between the needle protection element 7 and the housing 2. Any other spacer device to create a minimum distance between the needle protection element 7 and the housing 2 may also be applied.

When relative movement of the needle protection element 7 and the housing 2 towards each other is prevented by the spacer 27 or obstructed by the tissue in the space 18, movement of the operating portion 8 will result in a relative movement of the first needle holder part 10 with respect to the second needle holder part 11 resulting in the needles 9 being pushed by stop 13 in proximal direction. The free ends of the needles 9 will extend out of the needle protection element 7 and into the tissue to be sutured.

Figure 7:
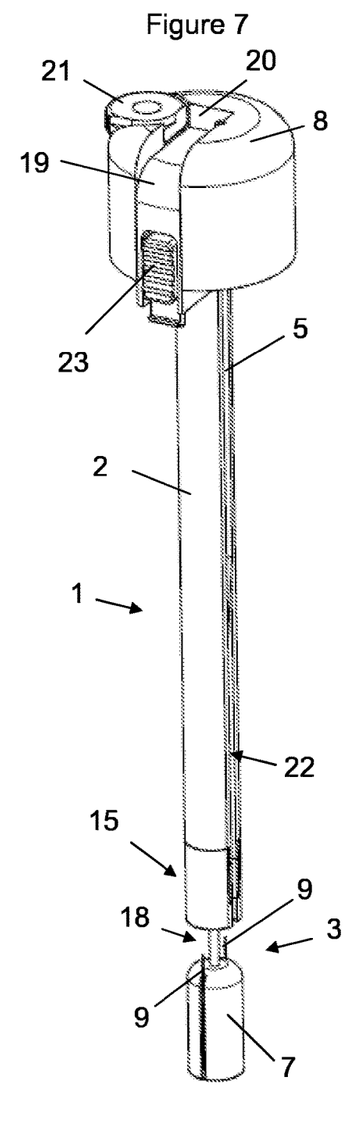
FIG. 7 shows the suture device of FIG. 1 with needles extending out of the needle protection element.

FIG. 7 shows the needles of the suture device 1 extending from the needle protection element 7 into the space 18 where, during actual use, the tissue to be sutured is arranged. This movement of the operating portion 8 in proximal direction may be continued until the free ends of the needles 9 are received by the needle receive device 15 and the opposite needle ends are released by the needle holder 6, in this case when the stop 13 reaches the recesses 14.

Figure 8:
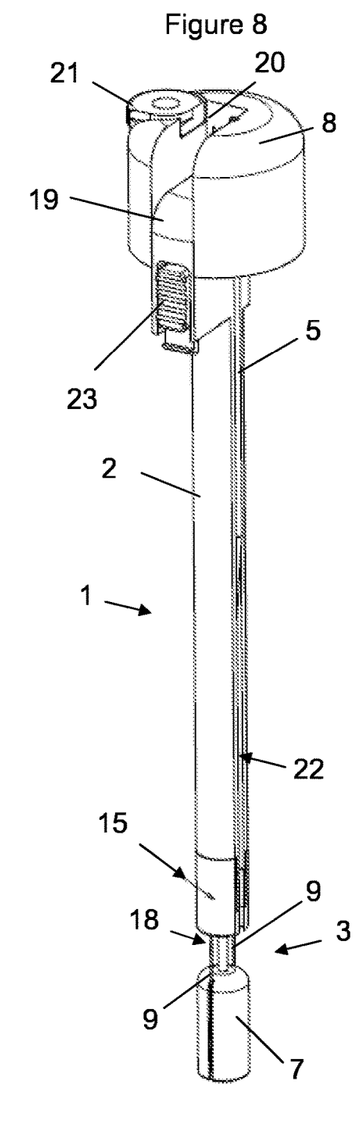
FIG. 8 shows the suture device of FIG. 1 with needles transferred to the needle receive device.

The suture device 1 is now arranged in the needle transfer position, wherein the needles 9 are transferred from the needle holder 6 to the needle receive device 15. FIG. 8 shows the suture device 1 in the needle transfer position. It is remarked that the needle holder 6 and the needles 9 during transfer of the needles from the insertion position to the needle transfer position did not enter any space, other than space 18, which was not yet within the contour of the suture device 1 before this movement. This reduces substantially the risk of damaging any tissue or portion within the body during this movement.

As the needles 9 are transferred from the needle holder 6 to the needle receive device 15, the needles 9 extend through the tissue. By pulling the needles 9 further through the tissue, suture material connected to the needles can also be pulled through the tissue. To pull the needles through the tissue the operating part 19 of the housing can be unlatched from the trocar 100 by pushing the associated pivotable push button 23.

Before the housing 2 is uncoupled from the trocar 100, the needle operating device 3 may be moved back in the distal direction and the operating portion 8 may be recoupled to the trocar 100 before uncoupling of the operating part 19. This has the advantage that the needles are completely moved out of the needle holder 6 and needle protection element 7. Further, by recoupling the operating portion 8 to the trocar 100 the rotational position of the needle holder can be maintained. This may decrease the chance that the suture material is twisted. This is desirable as the twisted suture material may hinder the removal of the needle operating device 3 through the puncture wound.

Once the operating part 19 is uncoupled from the trocar 100, the housing 18 can be pulled out of the trocar 100 in proximal direction, therewith pulling the needles 9 out of the needle operating device 3.

Figure 9:
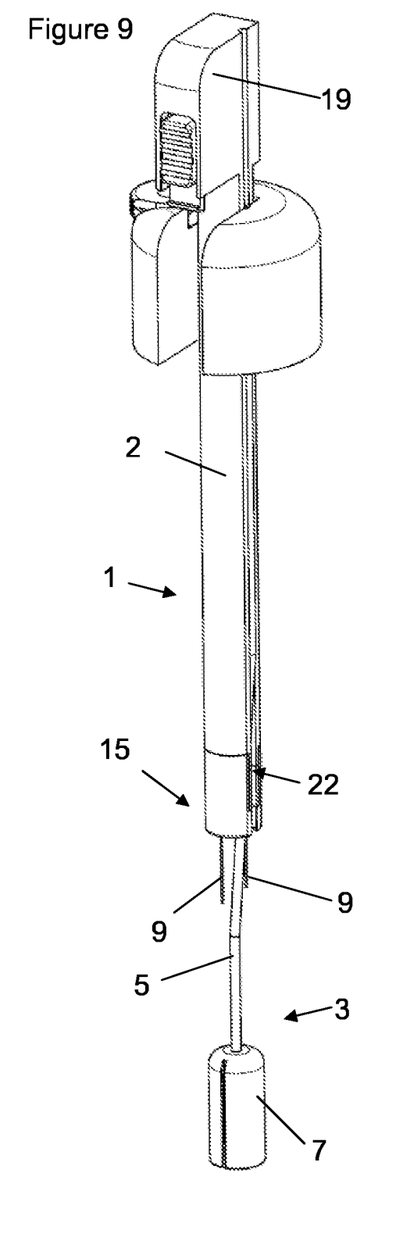
FIG. 9 shows the suture device of FIG. 1, wherein the housing is partly moved in the proximal direction with respect to the needle operating device.
Figure 10:
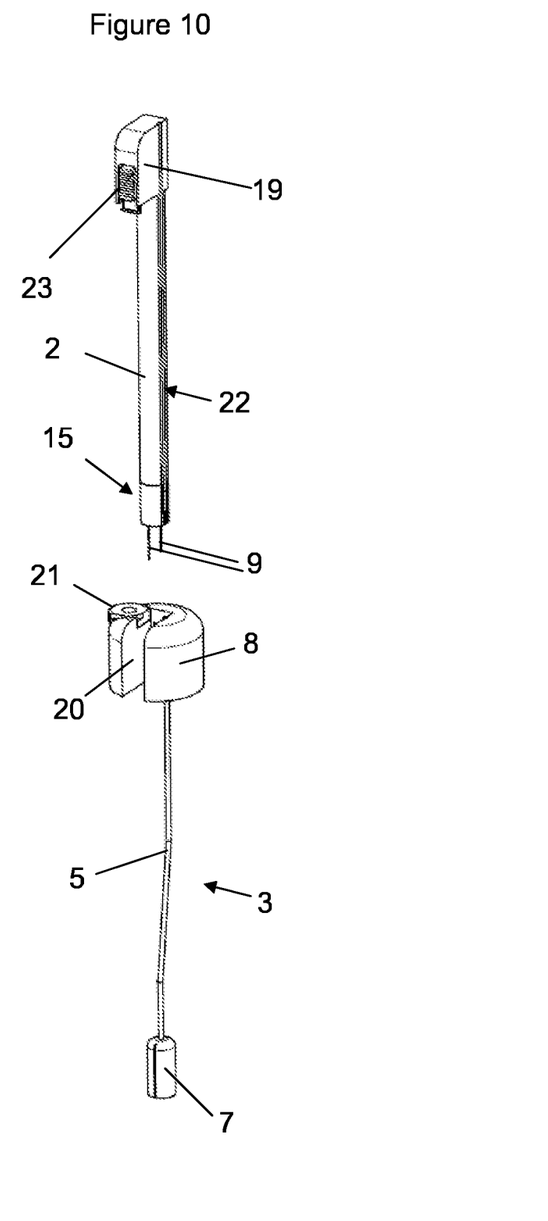
FIG. 10 shows the suture device of FIG. 1, wherein the housing is completely taken out of the needle operating device.

FIG. 9 shows the housing 2 being pulled in the proximal direction, and FIG. 10 shows the housing completely moved out of contact with the needle operating device 2. Since the operating element 5 is arranged in an open channel 21, the housing 2 can be pulled in proximal direction without having to remove the operating element 5 from it position. During the proximal movement of the housing 2, the operating element 5 will be pulled out of the holding device 24.

Suture material will be pulled together with the needles 9 through the tissue to be sutured and out of the patient's body. Normally, the suture material will be connected to both needles 9. The suture material to be released during the proximal movement of the housing out of the patient's body may be stored in a storage space in the suture device 1. In the embodiment shown in FIGS. 1 and 2, the suture material can be stored in a hollow channel 25 in the operating element 5, as shown in FIG. 5*a*.

Figure 12:
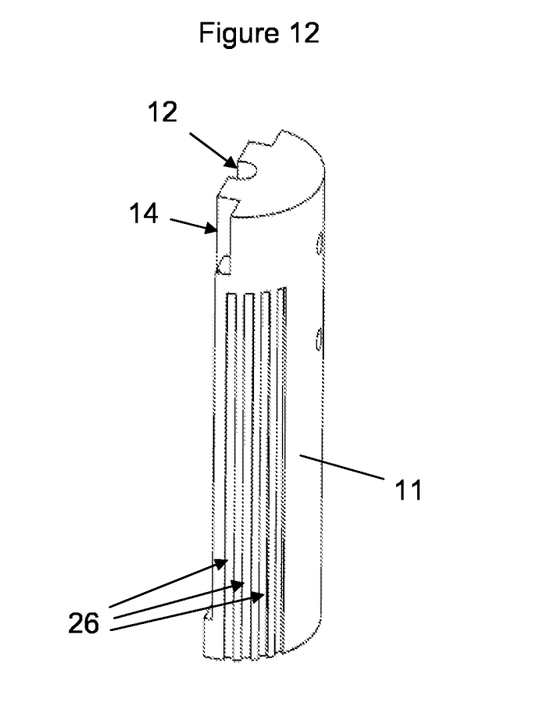
FIG. 12 shows an embodiment of a storage space for suture material.

FIG. 12 shows an alternative embodiment of a storage space for suture material. In this embodiment, the suture material may be stored in a number of grooves 26 in the second needle holder part 11. Other storage spaces may also be provided for storage of the suture material.

Once the needles 9 are retrieved from the patient's body, the needle operating device 3 may be pulled out of the trocar 100. In an alternative embodiment, the needle operating device 3 may be removed together with the housing after a first proximal movement of the housing, in particular when the needles 9 are completely pulled out of the tissue to be sutured.

The loop of suture material at the internal side of the tissue to be sutured will remain within the patient's body. When the needle operating device 2 and the trocar 100 are removed, the puncture wound can be closed by placing a knot in the suture material. The needles may be cut off from the suture material before or after the knot has been made in the suture material.

Hereinabove, an embodiment of a suture device according to the invention is described. In this embodiment, the suture device 1 is proposed to be used in combination with a trocar. However, the suture device 1 may also be used to suture a wound, when no trocar is present in the wound. In such case the suture device may be moved, in its insertion position, into the puncture wound until the tissue material enters the space 18. Also, in this insertion direction the entering of the tissue material into the space 18 can well be felt by the surgeon using the suture device 1.

In an alternative embodiment, it may be possible that a separate cannula device is provided which is first introduced into the wound before the suture device 1 is introduced, or a cannula device can be introduced together with the suture device 1.

The invention can be embodied in various other embodiments without departing from the scope of the invention. Therefore, the embodiment described above is illustrative only and is not intended to limit the invention, as a matter of course.

The invention claimed is:

1. A suture device, comprising a needle operating device and an elongate housing, wherein the needle operating device is movable in a longitudinal direction with respect to the housing between at least an insertion position and a needle transfer position, wherein the needle operating device comprises:
   an elongate operating element configured to extend from a distal end of the housing to or near a proximal end of the housing;
   a needle holder connected at a distal end of the operating element and configured to hold two or more needles at opposite sides of the operating element, such that free ends of the needles are directed in a proximal direction of the suture device; and a needle protection device, wherein the needle holder is at least partially movable with respect to the needle protection device between at least a protecting position wherein at least the free ends of the needles held by the needle holder are shielded by the needle protection device, and a non-protecting position wherein the free ends of the needles are not shielded by the needle protection device, wherein the housing comprises a needle receive device configured at a distal end of the housing to receive the free ends of the needles when the needle operating device is moved from the insertion position to the needle transfer position, wherein the elongated operating element is operatively joined to the two or more needles such that relative movement between the elongated operating element and the housing causes simultaneous displacement of the two or more needles and at least part of the needle holder, and wherein in at least the insertion position of the needle operating device, the needle holder and the needle protection device are spaced from the housing in the longitudinal direction to receive a tissue to be sutured therebetween.

2. The suture device of claim 1, wherein, when in the insertion position, a cross sectional dimension of the operating element between the housing and the needle holder is smaller than a cross sectional dimension of the needle holder and a cross-sectional dimension of the housing.

3. The suture device of claim 1, wherein the suture device comprises two or more needles.

4. The suture device of claim 3, wherein the needles are straight needles arranged substantially parallel to and at opposite sides of a longitudinal axis of the housing.

5. The suture device of claim 1, wherein the housing comprises a longitudinal open channel to enclose the operating element.

6. The suture device of claim 1, wherein the needle holder comprises a first needle holder part and a second needle holder part, wherein the first and second needle holder parts are configured to hold the needles therebetween, wherein the first needle holder part is operatively connected to the operating element, and wherein the second needle holder part supports the needle protection device, and wherein the first and second needle holder parts are movable with respect to each other in order to displace the needles with respect to the needle protection device and to release the needles from the needle holder when the free ends of the needle are received by the needle receive device.

7. The suture device of claim 1, wherein the needle receive device comprises a sleeve and a flexible disc-shaped element configured in the sleeve, wherein the sleeve and the disc shaped element and are designed to catch a needle therebetween.

8. The suture device of claim 1, wherein the suture device comprises one or more coupling elements to couple the suture device to a trocar.

9. The suture device of claim 8, wherein a first coupling element is provided on the housing to couple the housing to the trocar, and wherein a second coupling element is provided on the needle operating device to couple the needle operating device to the trocar.

10. The suture device of claim 1, wherein the suture device comprises a positioning part having a non-circular cross section to determine a rotational position of the needle operating device and/or the housing with respect to a non-circular puncture in which the suture device is arranged.

11. The suture device of claim 10, wherein the positioning part is arranged in a space between needle holder and needle receive device or at the distal end of the suture device.

12. The suture device of claim 1, wherein the needle holder comprises a suture material storage space for storing suture material.

13. The suture device of claim 1, wherein the needle operating device and the housing are constrained in a rotational position with respect to each other.

14. The suture device of claim 1, wherein the needle protection device is a sleeve element.

15. The suture device of claim 1, wherein the suture device comprises a spacer device configured to ensure a minimum distance between the needle protection device and the housing.

16. The suture device of claim 1, wherein, in at least the insertion position of the needle operating device, the operating element extends substantially along a longitudinal axis of the suture device in a space between the housing and the needle holder and the needle protection device so that the space has substantially the same volume at opposite sides of the operating element.

17. A combination of a suture device according to claim 1 and a trocar or a cannula device, wherein the trocar or the cannula device and suture device are configured to be coupled to each other in a fixed rotational position.

18. A suture device, comprising a needle operating device and an elongate housing, wherein the needle operating device is movable in a longitudinal direction with respect to the housing between at least an insertion position and a needle transfer position, wherein the needle operating device comprises:

an elongate operating element configured to extend from a distal end of the housing to or near a proximal end of the housing;

a needle holder connected at a distal end of the operating element holding two or more straight needles at opposite sides of the operating element and a longitudinal axis of the housing, such that free ends of the needles are directed in a proximal direction of the suture device; and a needle protection device, wherein the needle holder is at least partially movable with respect to the needle protection device between at least a protecting position wherein at least the free ends of the needles held by the needle holder are shielded by the needle protection device, and a non-protecting position wherein the free ends of the needles are not shielded by the needle protection device, wherein the housing comprises a needle receive device configured at a distal end of the housing to receive the free ends of the needles when the needle operating device is moved from the insertion position to the needle transfer position, wherein the elongated operating element is operatively joined to the two or more straight needles such that relative movement between the elongated operating element and the housing causes simultaneous displacement of the two or more straight needles and at least part of the needle holder, and wherein in at least the insertion position of the needle operating device, the needle holder and the needle protection device are spaced from the housing in the longitudinal direction to receive a tissue to be sutured therebetween.

19. A suture device, comprising a needle operating device and an elongate housing, wherein the needle operating device is movable in a longitudinal direction with respect to the housing between at least an insertion position and a needle transfer position, wherein the needle operating device comprises:

an elongate operating element configured to extend from a distal end of the housing to or near a proximal end of the housing;

a needle holder connected at a distal end of the operating element and configured to hold two or more needles at opposite sides of the operating element, such that free ends of the needles are directed in a proximal direction of the suture device; and a needle protection device, wherein the needle holder is at least partially movable with respect to the needle protection device between at least a protecting position wherein at least the free ends of the needles held by the needle holder are shielded by the needle protection device, and a non-protecting position wherein the free ends of the needles are not shielded by the needle protection device, wherein the housing comprises a needle receive device configured at a distal end of the housing to receive the free ends of the needles when the needle operating device is moved from the insertion position to the needle transfer position, and wherein in at least the insertion position of the needle operating device, the needle holder and the needle protection device are spaced from the housing in the longitudinal direction to receive a tissue to be sutured therebetween, wherein the suture device comprises a positioning part having a non-circular cross section to determine a rotational position of the needle operating device and/or the housing with respect to a non-circular puncture in which the suture device is arranged, the non-circular cross section of the positioning part defining a longest dimension and the needles being arranged on a line perpendicular to the direction of the longest dimension.

20. The suture device of claim 19, wherein the positioning part is arranged in a space between the needle holder and the needle receive device or at the distal end of the suture device.

21. The suture device of claim 19, wherein a cross sectional dimension of the positioning part is smaller than a cross sectional dimension of the needle holder and a cross-sectional dimension of the housing.

22. The suture device of claim 19, wherein the needles are straight needles arranged substantially parallel to a longitudinal axis of the housing.

23. The suture device of claim 19, wherein the needle holder comprises a first needle holder part and a second needle holder part, wherein the first and second needle holder parts are configured to hold the needles therebetween, wherein the first needle holder part is operatively connected to the operating element, and wherein the second needle holder part supports the needle protection device, and wherein the first and second needle holder parts are movable with respect to each other in order to displace the needles with respect to the needle protection device and to release the needles from the needle holder when the free ends of the needle are received by the needle receive device.

24. The suture device of claim 19, wherein the needle operating device and the housing are constrained in a rotational position with respect to each other.

* * * * *